US008802914B2

(12) United States Patent
Corradi

(10) Patent No.: US 8,802,914 B2
(45) Date of Patent: Aug. 12, 2014

(54) **PROCESS AND APPARATUS FOR *PARA*-XYLENE PRODUCTION USING MULTIPLE ADSORPTIVE SEPARATION UNITS AND A SPLIT FRACTIONATING COLUMN**

(75) Inventor: Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 88 days.

(21) Appl. No.: 13/327,029

(22) Filed: Dec. 15, 2011

(65) Prior Publication Data

US 2013/0158330 A1   Jun. 20, 2013

(51) Int. Cl.
    *C07C 7/12* (2006.01)
(52) U.S. Cl.
    USPC ........... 585/828; 585/805; 585/820; 585/822; 585/825; 585/826
(58) Field of Classification Search
    None
    See application file for complete search history.

(56) References Cited

U.S. PATENT DOCUMENTS

| | | | |
|---|---|---|---|
| 4,039,599 A | | 8/1977 | Gewartowski |
| 4,381,419 A | * | 4/1983 | Wylie .............................. 585/828 |
| 5,177,295 A | | 1/1993 | Oroskar et al. |
| 5,763,714 A | | 6/1998 | Hickey et al. |
| 6,369,287 B1 | | 4/2002 | Magne-Drisch et al. |
| 6,407,303 B1 | | 6/2002 | O'Brien et al. |
| 6,483,002 B1 | | 11/2002 | O'Brien |
| 7,687,674 B2 | | 3/2010 | Wegerer |
| 7,915,471 B2 | | 3/2011 | Leflaive et al. |
| 7,977,526 B2 | | 7/2011 | Porter |
| 8,008,536 B2 | | 8/2011 | Winter et al. |
| 2009/0069612 A1 | | 3/2009 | Hotier et al. |
| 2009/0234170 A1 | * | 9/2009 | Lee et al. ...................... 585/470 |

OTHER PUBLICATIONS

Lacosse, et al., BTX production: Flexibility through modern UOP Technology, Hydrocarbon Technology International, 125-28, 1993.
D'Auria, et al., Produce para-xylene economically, Chem Systems Annual US Chemical Conference (Houston Jan. 29-30, 1997), Fuel Technology & Management, 7 (3): 35-36,38,40-41, 1997.
Basak, Aromatics & Down Stream Process, GM(PC), IOCL-RHQ, IndianOil.
International Search Report for PCT/US2012/059171 dated Mar. 14, 2013.

* cited by examiner

*Primary Examiner* — Tam M Nguyen
(74) *Attorney, Agent, or Firm* — Mark R Willis

(57) ABSTRACT

A process for separating para-xylene from a plurality of xylene isomers, wherein the process introduces at a first feed point a first mixed xylene stream comprising a plurality of xylene isomers into a first adsorptive separation unit to produce a first para-xylene enriched stream and a first raffinate stream, and introduces a second mixed xylene stream comprising a plurality of xylene isomers into a second adsorptive separation unit to produce a second raffinate stream. The process feeds both the first raffinate stream and the second raffinate stream into a raffinate column. The process further introduces an extract stream from the second adsorptive separation unit into a first input of a split extract column comprising an internal partition defining a first distillation zone and a second distillation zone.

7 Claims, 3 Drawing Sheets

PROCESS AND APPARATUS FOR PARA-XYLENE PRODUCTION USING MULTIPLE ADSORPTIVE SEPARATION UNITS AND A SPLIT FRACTIONATING COLUMN

FIELD OF THE INVENTION

The disclosure relates to a process for the formation and adsorptive separation of a select xylene isomer, preferably para-xylene, from a feed stream containing a mix of aromatic and non-aromatic hydrocarbons. More specifically, the disclosure relates to increasing the efficiency of para-xylene production by eliminating the need to vaporize the product stream from the isomerization process. Most specifically, the disclosure relates to a para-xylene process comprising multiple adsorptive separation units, each using a different desorbent, to eliminate fractional distillation of the isomerized product stream, and a split fractionation column to consolidate multiple fractionation columns.

BACKGROUND OF THE INVENTION

Para-xylene, an aromatic hydrocarbon, is an important intermediate which finds wide and varied application in chemical syntheses. Upon oxidation, para-xylene yields terephthalic acid. Polyester fabrics and resins are produced from a polymer of ethylene glycol and terephthalic acid. These polyester materials are used extensively in a number of industries and are used to manufacture such items as, for example, clothing, beverage containers, electronic components, and insulating materials.

The production of para-xylene is practiced commercially in large-scale facilities and is highly competitive. Concerns exist not only about the effective conversion of feedstock through one or more of isomerization, transalkylation and disproportionation to produce para-xylene and effective separation of para-xylene from the resultant mixture of C8 aromatic isomers, but also with the energy costs and capital costs associated with such processes.

In prior art processes, C9 aromatics are separated from the C8 aromatics, i.e., xylene isomers, by fractional distillation. This requires heating of the admixture to vaporize the C8 and lighter aromatics. A large portion of the isomerization stream must be vaporized to accomplish the C9 separation because the stream is generally composed primarily of C8 and lighter aromatics. This separation requires a substantial amount of energy and associated cost. After the C9 aromatic removal, the C8-containing stream is then recycled into the adsorptive separation unit.

Accordingly, it would be an advance in the state of the art to provide a process for the production of para-xylene, including separation and isomeric formation from an admixture of C8 aromatic isomers, that removes the need to vaporize the isomerized stream for removal of C9 aromatics, thereby lowering operational expenses, in the form of energy consumption, and capital expenditures, in the form of required processing equipment and the size of such processing equipment. It would be a further advance in the state of the art to share a fractionation column between the aromatic conversion process and the xylene separation process, thereby reducing capital costs.

SUMMARY OF THE INVENTION

A process for separating para-xylene from a plurality of xylene isomers is presented. The process introduces at a first feed point a first mixed xylene stream comprising a plurality of xylene isomers into a first adsorptive separation unit to produce a first para-xylene enriched stream and a first raffinate stream, and introduces a second mixed xylene stream comprising a plurality of xylene isomers into a second adsorptive separation unit to produce a second raffinate stream.

The process feeds both the first raffinate stream and the second raffinate stream into a raffinate column. The process further introduces an extract stream from the second adsorptive separation unit into a first input of a split extract column comprising an internal partition defining a first distillation zone and a second distillation zone. The split extract column comprises a first input for a first distillation zone, a second input for a second distillation zone, a first output for the first distillation zone, and a second output for the second distillation zone.

A fractional distillation column is presented. The factional distillation column comprises a housing, a partition disposed within the housing, where that partition defines a first distillation zone and a second distillation zone. The fractional distillation column further comprises a first input port formed to extend through the housing and into the first distillation zone, a first output port formed to extend outwardly from the first distillation zone and through the housing, a second input port formed to extend through the housing and into the second distillation zone, and a second output port formed to extend outwardly from the second distillation zone and through the housing.

An apparatus for separating para-xylene from a plurality of xylene isomers is presented. The apparatus comprises a first adsorptive separation unit, a second adsorptive separation unit, a raffinate column in fluid communication with both the first adsorptive separation unit and the second adsorptive separation unit. The apparatus further comprises Applicant's fractional distillation column in fluid communication with the second adsorptive separation unit.

DETAILED DESCRIPTION OF PREFERRED EMBODIMENTS

Figure 1:
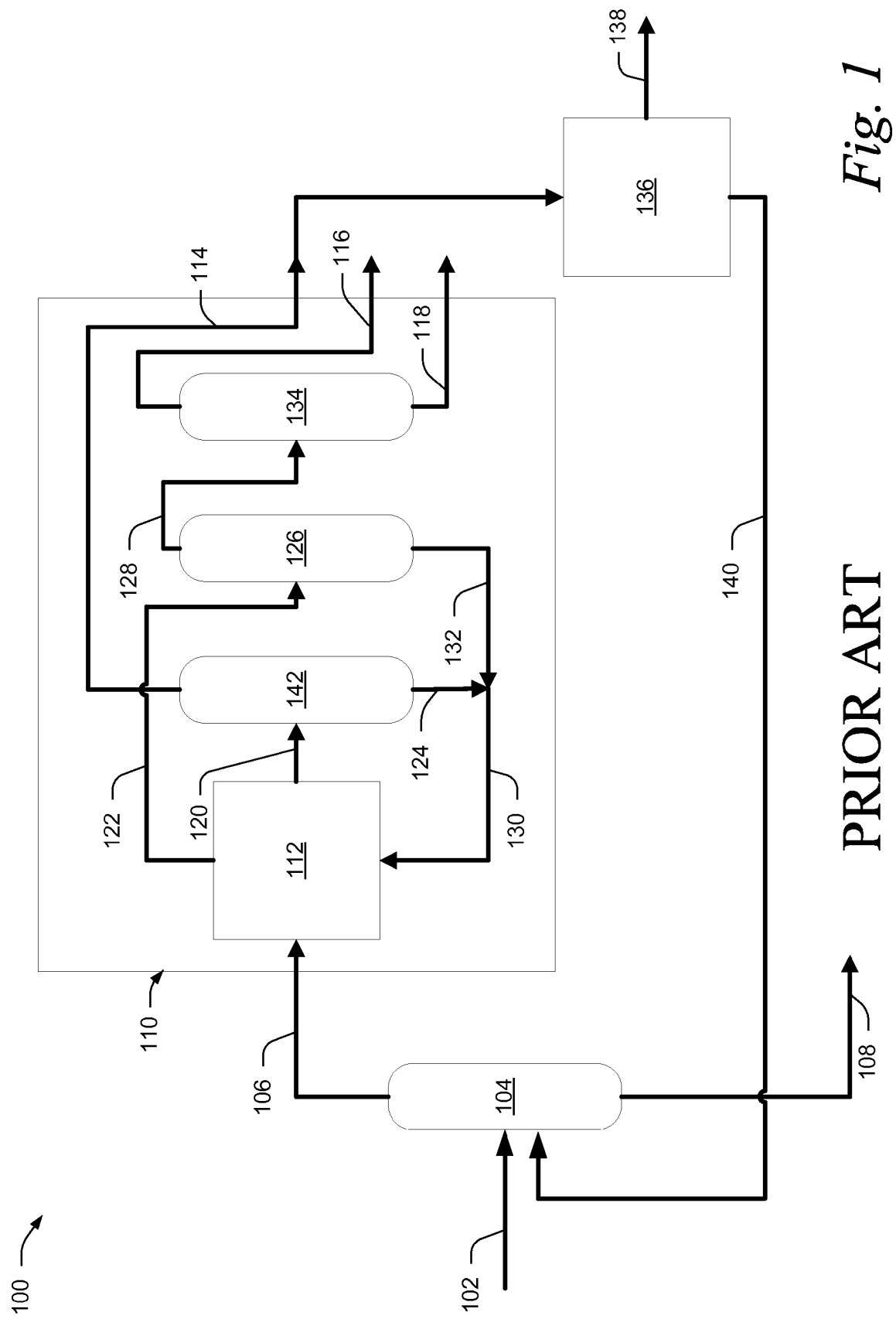
FIG. 1 is a diagram of a prior art process.

Para-xylene is typically recovered from a mixed aromatic hydrocarbon fraction derived from various sources such as catalytic reforming by liquid-liquid extraction and/or fractional distillation. The para-xylene is commercially separated from a feed stream that typically contains all three xylene isomers, namely ortho-xylene, meta-xylene, and para-xylene. The para-xylene, or other desired isomer, is separated by either fractional crystallization or adsorptive separation or a combination of these two techniques. Adsorptive separation is generally preferred as it has a significantly higher single pass recovery (~97%) relative to crystallization separation (~65%).

A typical adsorptive separation process first involves the separation of C8 aromatic hydrocarbons, including ortho-xylene, meta-xylene, para-xylene, and ethylbenzene, from heavier aromatic hydrocarbons (i.e., C9+) and non-aromatic hydrocarbons through fractional distillation.

Those skilled in the art will appreciate that the designator "CX" refers to a compound comprising X carbon atoms, "CX+" refers to a compound comprising X or greater carbon atoms, and "CX−" refers to a compound comprising X or fewer carbon atoms.

The para-xylene isomers are then separated from the C8 isomer admixture using a simulated countercurrent moving-bed (SMB) adsorptive separation unit. This simulation is performed using established commercial technology wherein an adsorbent, commonly a solid zeolitic material, is held in place in one or more cylindrical adsorbent chambers. The positions at which the streams involved in the process enter and leave the chamber(s) are slowly shifted along the height of the chamber(s). Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals in a step-wise manner. Each shift in location of these transfer points delivers or removes liquid from a different bed within the chamber.

A typical chamber has a single line for each bed. The flow into or out of a particular line, as the case may be, is controlled by a rotary valve. The shifting of streams along the bed simulates movement of the absorbent in a direction opposite the flow of liquid, even though the absorbent is fixed in place within the chamber. SMB chambers are also well suited for high volume production because the input and output streams have nearly constant compositions throughout simulated motion of the absorbent material in the bed.

A typical SMB unit recycles a heavy desorbent, such as para-diethylbenzene, to separate high purity para-xylene from the other C8 isomers. Para-diethylbenzene is a C10 aromatic that is separated from para-xylene by fractional distillation.

The admixture of non-para-xylene isomers from the adsorptive separation unit is subjected to catalytic isomerization to reestablish an equilibrium amount of para-xylene isomers in the admixture. In addition to para-xylene and other C8 isomers, the isomerized stream typically contains an amount of C9+ aromatics, which will accumulate in the desorbent and, therefore, must be removed.

Processes for isolating a desired isomer of xylene without the vaporization of the full isomerized product stream are presented. The process comprises two adsorptive separation units. The first unit utilizes a heavy desorbent and the second unit utilizes a light desorbent. Those skilled in the art will appreciate that a desorbent used in combination with a simulated moving bed absorbent system facilitates removal of an absorbed material from the adsorbent bed. This being the case, a useful desorbent will have an affinity for the desired material, i.e., para-xylene, that is substantially the same as the affinity of the adsorbent bed for that desired material.

As used herein, the terms heavy and light are generally in reference to the boiling point of the desorbent relative to the C8 aromatics, namely, ortho-, meta-, para-xylene and ethylbenzene.

In certain embodiments, the heavy desorbent is selected from the group consisting of para-diethylbenzene, para-diisopropylbenzene, tetralin, and the like, and combinations thereof. In certain embodiments, toluene and the like can be used as the light desorbent. The para-diethylbenzene has a higher boiling point than the C8 aromatic isomers and, as such, the para-diethylbenzene is the bottoms (i.e., heavy) product when separated from the C8 isomers in a fractional distillation column. Similarly, toluene has a lower boiling point than the C8 aromatic isomers and, as such, the toluene is the overhead (i.e., light) product when separated from the C8 isomers in a fractional distillation column.

Unlike prior art processes, Applicant's process comprises feeding a stream of material containing a desired xylene isomer formed in an isomerization unit into a second adsorptive separation unit, as opposed to being fed back into a fractional distillation column. An extract stream from the second adsorptive separation unit, rich in the desired xylene isomer, is fed back into a first adsorptive separation unit for isolation of the desired xylene isomer. The process is presented in greater detail below.

Referring to FIG. 1, a diagram 100 of a prior art process for the production of para-xylene is depicted. A feed stream 102 enters a xylene fractionation unit 104. The feed stream typically contains ortho-, meta-, and para-xylene isomers and may also contain quantities of ethylbenzene, toluene, C8 cycloalkanes, alkanes, and hydrocarbons having more than eight carbon atoms per molecule.

The xylene fractionation unit 104 is a fractional distillation column. The xylene fractionation unit 104 divides the incoming stream into an overhead stream 106 comprising the C8 and lighter aromatics, including the xylene isomers, ethylbenzene, and toluene, and a bottoms 108 and one or more side cut streams (not shown) comprising C9+ aromatics.

Table 1 recites an example composition for feed stream 102.

TABLE 1

| Component | Amount |
| --- | --- |
| para-xylene | 10-20 wt % |
| Total C8 Aromatics | 25-60 wt % |
| ethylbenzene | 10-20 wt % |
| toluene | 0.5-2.0 wt % |
| C9+ | 25-30 wt % |
| Nonaromatic hydrocarbons | <0.5 wt % |
| Nitrogen | 1.0 mg/kg |
| Sulfur | 1.0 mg/kg |

The overhead stream 106 enters the separation assembly 110, where the input stream 106 is separated into a raffinate stream 114, a toluene stream 116, and a para-xylene stream 118. The raffinate stream 114 has been substantially depleted of para-xylene but contains other C8 aromatics, including ortho-xylene, meta-xylene and ethylbenzene.

Within the separation assembly 110, the stream 106 enters an adsorptive separation unit 112. The adsorptive separation unit 112 separates the incoming stream 106 into a raffinate stream 120 and an extract stream 122. The adsorptive separation unit 112 typically comprises two SMB chambers and a rotary valve. Each individual chamber typically has 12 beds. A bedline connects each bed to the rotary valve. The rotary valve controls the flow of material into or out of each SMB chamber in a step-wise manner to create a simulated moving bed.

A heavy desorbent, typically para-diethylbenzene, is used to facilitate the separation of the raffinate stream 120 and extract stream 122. The raffinate stream 120 comprises ethylbenzene, meta-xylene, and ortho-xylene diluted with desorbent and any heavies. Heavies are hydrocarbons with a boiling point greater than that of the C8 aromatic isomers and include C9+ aromatics. The extract stream 122 comprises para-xylene diluted with desorbent and light ends. Light ends are hydrocarbons with a boiling point below that of the C8 aromatic isomers and include toluene and other C7− aromatics.

The raffinate stream 120 is directed to a raffinate column 142. The raffinate column 142 is a fractional distillation column that divides the incoming stream 120 into (i) an overhead raffinate stream 114 comprising ethylbenzene, meta-xylene, and ortho-xylene and (ii) a bottoms stream 124 comprising desorbent and any heavies. The bottoms stream 124 is recycled back to the adsorptive separation unit 112 through combined stream 130. The overhead raffinate stream 114 is directed to an isomerization unit 136.

The extract stream 122, comprising xylene isomers and ethylbenzene, enters extract column 126. Extract column 126 is a fractional distillation column that divides the incoming stream 122 into (i) an overhead stream 128 comprising para-xylene and toluene and (ii) a bottoms stream 132 comprising desorbent and heavies. The bottoms stream 132 containing desorbent is recycled back to the adsorptive separation unit 112 through combined stream 130. Heavies in the combined desorbent stream 130 may be removed by directing a slipstream of the desorbent into a small desorbent rerun column.

The overhead stream 128, comprising para-xylene and toluene, enters finishing column 134. Finishing column 134 is a fractional distillation column that divides the incoming stream 128 into (i) an overhead toluene stream 116 and (ii) a bottoms para-xylene stream 118. The bottoms para-xylene stream 118 contains the final desired product.

The raffinate stream 114 comprising ethylbenzene, meta-xylene, and ortho-xylene enters an isomerization unit 136. Catalysts in the isomerization unit 136 reestablish an equilibrium mixture of the ortho-, meta-, and para-xylene isomers and convert the ethylbenzene into xylenes and/or benzene.

Nonaromatic compounds in the raffinate stream 114 are cracked to light ends and removed in stream 138 along with any benzene. The isomerization process also creates quantities of C9+. The output stream 140 comprises an equilibrium mixture of xylene isomers as well as quantities of C9 aromatics and unreacted ethylbenzene. The output stream 140 is recycled back into the xylene fractionation unit 104.

The C9 aromatics produced during isomerization are separated from the C8 isomers in the xylene fractionation unit 104. While the C9 aromatics are only a very small portion of the stream, the entire C8 fraction must be vaporized to accomplish this separation.

Figure 2:
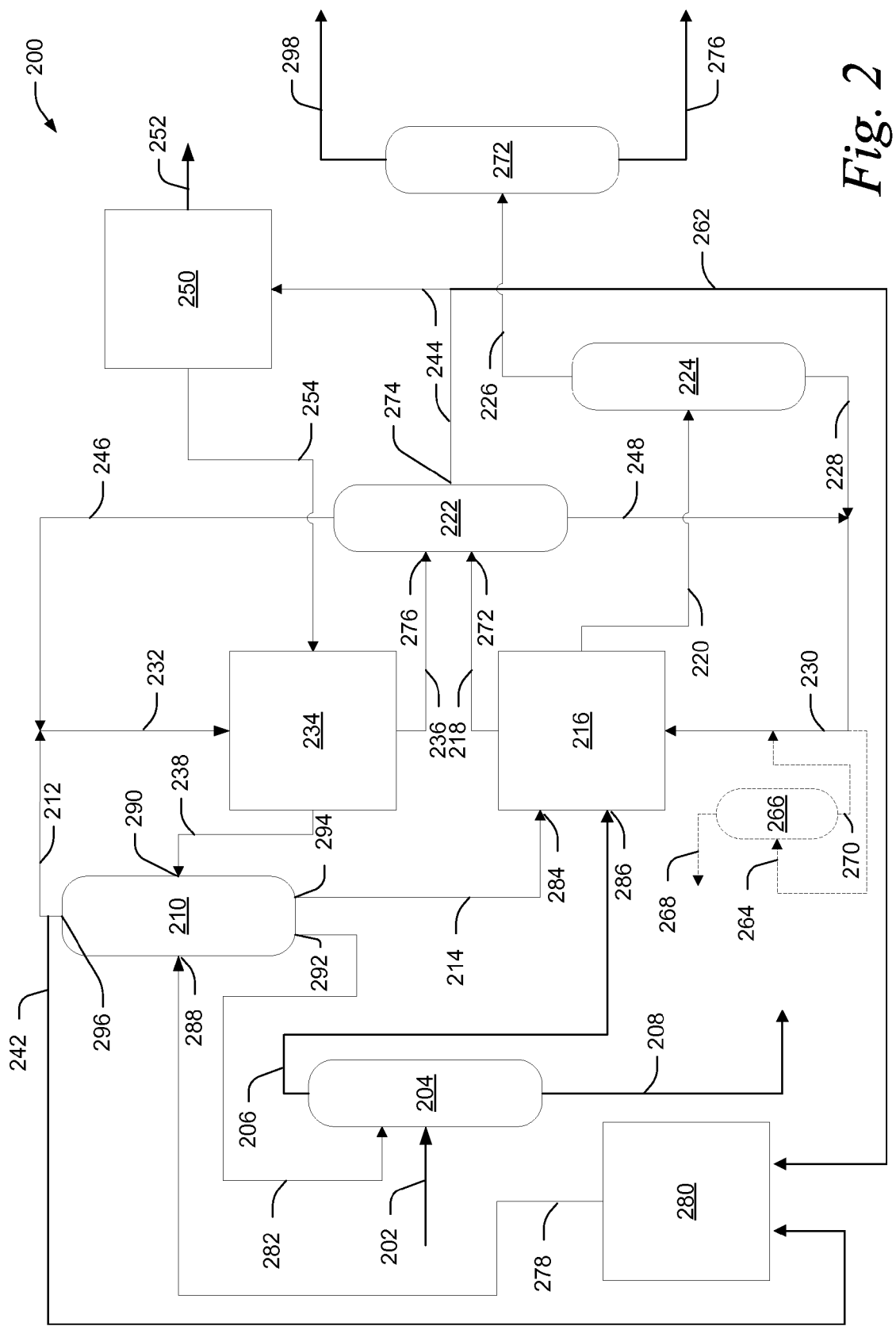
FIG. 2 is a diagram of one embodiment of the disclosed process having a split fractionation column where light impurities are removed early in the process and a drag stream is fed into an aromatic conversion assembly.

FIG. 2 illustrates embodiment 200 of Applicant's apparatus and process. A feed stream 202 enters a xylene fractionation unit 204. In one embodiment, the feed stream 202 contains ortho-, meta-, and para-xylene isomers. In one embodiment, the feed stream 202 contains quantities of ethylbenzene, toluene, C8 cycloalkanes, alkanes, and hydrocarbons having more than eight carbon atoms per molecule.

In one embodiment, the feed stream 202 is a result of hydrotreating naphtha to remove any sulfur and nitrogen contaminants and the subsequent catalytic reforming where paraffins and naphthenes in the decontaminated naphtha are converted to aromatics. The most light ends and C7− fractions are removed in a debutanizer and fractional distillation column, respectively. The feed stream 202, comprising a C8+ fraction, enters the xylene fractionation unit 204. In one embodiment, the feed stream 202 comprises about 23 weight percent para-xylene.

The xylene fractionation unit 204 is a fractional distillation column. The xylene fractionation unit 204 divides the incoming stream into an overhead stream 206 comprising the C8− aromatics, including the xylene isomers, ethylbenzene, and toluene, and a bottoms stream 208 and one or more side cut streams (not shown) comprising C9+ aromatics.

The overhead stream 206 from xylene fractionation unit 204, and bottoms stream 214 from extract column 210, enter adsorptive separation unit 216 at a first feed input 286 and a second feed input 284, respectively. Adsorptive separation unit 216 separates the incoming streams 206 and 214 into a raffinate stream 218 and an extract stream 220. In one embodiment, the heavy desorbent para-diethylbenzene is used to facilitate the separation of the raffinate stream 218 and extract stream 220. In certain embodiments, the heavy desorbent is selected from the group consisting of para-diethylbenzene, para-diisopropylbenzene, tetralin, and the like, and combinations thereof. The raffinate stream 218 comprises ethylbenzene, meta-xylene, and ortho-xylene diluted with desorbent. The extract stream 220 comprises para-xylene diluted with desorbent.

In one embodiment, adsorptive separation unit 216 comprises an SMB assembly and a rotary valve. In other embodiments, the adsorption separation unit 216 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of the SMB assembly in a step-wise manner to create a simulated moving bed and to flush the bed lines between flows of differing materials.

As a mixture of xylene isomers is fed into adsorptive separation unit 216, and flows downwardly, the mixture of xylene isomers contacts a solid adsorbent within the chamber. The zeolitic adsorbents disposed in adsorptive separation unit 216 have an affinity for para-xylene. As the mixture of xylene isomers flows over the solid adsorbent, the para-xylene is selectively adsorbed into the adsorbent while the other isomers continue to travel downward in the chamber in the bulk liquid.

In certain embodiments, the selectivity of the adsorbent in the adsorptive separation unit 216 for C7− aromatics is very close to that of para-xylene. As such, the C7− aromatics exit the adsorptive separation unit 216 by way of extract stream 220.

The extract stream 220 enters the extract column 224. Extract column 224 is a fractional distillation column that separates the incoming stream 220 into (i) an overhead para-xylene stream 226 comprising para-xylene, C7− aromatics, and light ends and (ii) a bottoms stream 228 comprising a heavy desorbent fraction, such as para-diethylbenzene, a C10 aromatic. The bottoms stream 228 is recycled back to the adsorptive separation unit 216 through combined stream 230.

Light desorbent enters adsorptive separation unit 234 by way of combined stream 232. Adsorptive separation unit 234 separates an incoming stream 254 into a raffinate stream 236 and an extract stream 238. Stream 254 is an isomerized stream from isomerization unit 250 comprising an equilibrium mixture of xylene isomers.

In one embodiment, the light desorbent toluene is used to facilitate the separation of the raffinate stream 236 and extract stream 238. In another embodiment, a light desorbent other than toluene is used to facilitate the separation of the raffinate stream 236 and extract stream 238. The raffinate stream 236 comprises ethylbenzene, meta-xylene, and ortho-xylene diluted with desorbent. The extract stream 238 comprises para-xylene diluted with desorbent.

In one embodiment, adsorptive separation unit 234 comprises an SMB assembly and a rotary valve. In other embodiments, the adsorption separation unit 234 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of the SMB assembly in a step-wise manner to create a simulated moving bed and to flush the bed lines between flows of differing materials.

As a mixture of xylene isomers is fed into adsorptive separation unit 234, and flows downwardly, the mixture of xylene isomers contacts a solid adsorbent within the chamber. The zeolitic adsorbents disposed in adsorptive separation unit 234 have an affinity for para-xylene. As the mixture of xylene isomers flows over the solid adsorbent, the para-xylene is selectively adsorbed into the adsorbent while the other isomers continue to travel downward in the chamber in the bulk liquid.

The raffinate stream 236 enters a raffinate column 222 at a third location 276.

The extract stream 238 and the output 278 from aromatic conversion unit 280 are fed into split extract column 210, a split fractional distillation column, at a first input 290 and second input 288, respectively.

The split extract column 210 separates the input streams into an overhead stream 212 at third output port 296 and a bottoms stream 214 and 282 at first output port 294 and second output port 292, respectively. The overhead stream 212/242 comprises primarily toluene. In one embodiment, stream 212/242 comprises also comprises C7– aromatics and light impurities. The bottoms stream 214 comprises C8 aromatic isomers, including a high concentration of para-xylene. The bottoms stream 282 comprises C8 aromatic isomers. In one embodiment, the bottoms stream 282 also comprises C9+ aromatics introduced by way of aromatics conversion unit 280. In one embodiment, the bottoms stream 282 has a lower concentration of para-xylene than does bottoms stream 214. The light desorbent, in one embodiment, toluene, is recycled in a light desorbent loop 212, 232, 238.

In one embodiment, a slipstream 242 is extracted from the overhead stream 212. In one embodiment, slipstream 242 prevents the accumulation of additional toluene introduced into the desorbent loop from the feed stream 202. In one embodiment, slipstream 242 prevents the accumulation of light impurities in the light desorbent loop. In one embodiment, slipstream 242 comprises high purity toluene. In one embodiment, slipstream 242 comprises toluene and light impurities from the feed stream 202.

Raffinate column 222 is a fractional distillation column that separates the raffinate stream 236 and 218, each comprising para-xylene depleted C8 aromatic isomers diluted with light and heavy desorbent, respectively, into a C8 aromatic isomer stream 244, a light desorbent stream 246, and a heavy desorbent stream 248. The C8 aromatic isomer stream 244 exits the raffinate column 222 at a second location 274.

The light desorbent along with any light impurities have the lowest boiling point and are, as such, extracted as a net overhead stream 246. The heavy desorbent along with any heavies have the highest boiling point and are, as such, extracted as a net bottoms stream 248. The ortho-xylene, meta-xylene, and ethylbenzene have an intermediate boiling point and are, as such, extracted at a sidecut tray. The heavy desorbent is recycled in a heavy desorbent loop 230, 220/218, 228/248.

In one embodiment, the C8 aromatic isomer stream 244 exits the raffinate column 222 at a location below that of raffinate stream 236 and above that of raffinate stream 218. In one embodiment, the raffinate stream 236 enters raffinate column 222 at a location on the column where the composition within the column 222 is similar to the composition in stream 236. In one embodiment, the raffinate stream 218 enters raffinate column 222 at a location on the column where the composition within the column 222 is similar to the composition in stream 218. As used herein, with reference to fractional distillation columns, the term "above" refers to a location in or on the column such that liquid inserted at the location will flow down toward the reference point. Similarly, the term "below" refers to a location in or on the column such that liquid inserted at the location will flow down away from the reference point.

The C8 aromatic isomer stream 244 comprising meta-xylene, ortho-xylene, and ethylbenzene enters an isomerization unit 250. Catalysts in the isomerization unit 250 reestablish an equilibrium mixture of the ortho-, meta-, and para-xylene isomers. In one embodiment, the catalyst is an ethylbenzene dealkylation catalyst, which converts ethylbenzene to a benzene co-product. In one embodiment, the catalyst is an ethylbenzene isomerization catalyst, which converts the ethylbenzene into additional xylene isomers.

Nonaromatic compounds in the C8 aromatic isomers stream 244 are cracked to light ends and removed in stream 252 along with any benzene co-product created. The isomerization process may also create small quantities of C9 and heavier aromatics. In one embodiment, the output stream 254 comprises an equilibrium mixture of xylene isomers. In one embodiment, the output stream 254 comprises small quantities of C9+ aromatics. In one embodiment, the output stream 254 comprises unreacted ethylbenzene.

In one embodiment, the output stream 254 comprises about 1.5 weight percent ethylbenzene or less. The isomerized output stream 254 enters adsorptive separation unit 234.

In certain embodiments, certain C9+ aromatics may be introduced by isomerization unit 250 and accumulate in the heavy desorbent loop 230, 220/218, 228/248. In certain configurations of the raffinate column 222, any C9 aromatics will accumulate in the isomerization loop 254, 236, 244. In other configurations of the raffinate column 222, any C9 aromatics will accumulate in the heavy desorbent loop 230, 220/218, 228/248. In yet other configurations of the raffinate column 222, any C9 aromatics will accumulate in both the isomerization loop and the heavy desorbent loop.

In different embodiments, one or more drag streams are used to prevent the accumulation of C9+ aromatics in the process. In one embodiment, if accumulation occurs in the heavy desorbent loop, a drag stream 264 is withdrawn from the desorbent loop by way of stream 230. Stream 230 comprises primarily heavy desorbent along with the C9 aromatic and heavy impurities. The drag stream 264 is fed into a fractional distillation column 266, which separates the drag stream 264 into an overhead stream 268 and a bottoms stream 270. The bottoms stream 270 comprises high purity para-diethylbenzene, which is returned to the desorbent loop by way of stream 230. In one embodiment, the amount of material withdrawn in drag stream 264 is about 1 to about 20 volume percent of stream 230.

In another embodiment, if accumulation occurs in the isomerization loop (i.e., 254, 236, 244), a drag stream 262 is withdrawn from the isomerization loop by way of raffinate stream 244. Stream 262 comprises a mixture of ortho-xylene, meta-xylene, ethylbenzene along with the C9 aromatic and heavy impurities. In one embodiment, the amount of material in the drag stream 262 is about 1 to about 20 volume percent of the raffinate stream 244.

In yet another embodiment, if the accumulation occurs in both the isomerization loop and the heavy desorbent loop, drag streams 262 and 264 are both used. In other embodiments, no drag streams are used. In other embodiments, the impurities are extracted by another process known in the art capable of separating C9 aromatics and heavies from para-diethylbenzene.

In one embodiment, the aromatic conversion unit 280 converts the incoming stream 262, comprising a mixture of toluene and C9+ aromatics, into an output stream 278 comprising an equilibrium mixture of xylene isomers, ethylbenzene and toluene. The aromatic conversion unit 280 facilitates catalytic disproportionation reactions, which convert toluene into a mixture of benzene and xylene isomers. The aromatic conversion unit 280 also facilitates catalytic transalkylation reactions, which convert a blend of toluene and C9 aromatic isomers to xylene isomers through the migration of methyl groups between methyl-substituted aromatics. Benzene produced in the aromatic conversion assembly is extracted in an additional stream (not shown).

The output stream 278 is fed into the split extract column 210, which separates the output stream 278 into an overhead stream comprising toluene and a bottoms stream 282 comprising C8+ aromatics. The bottoms stream 282 is fed back into the xylene fractionation column 204 to separate the C8 aromatics into stream 206 and the C9+ aromatics into stream 208.

The overhead toluene stream from the split extract column 210 is split into streams 212 and 242. Stream 242 is recycled back into the aromatic conversion unit 280 for transalkylation. Stream 212 is part of the light desorbent loop 212, 232, 238.

The finishing column 272 separates the overhead stream 226 from extract column 224 into an overhead stream 298 comprising C7− aromatics, and a bottoms stream 276 comprising high purity para-xylene.

In certain embodiments, para-ethyltoluene, structurally similar to para-xylene, may be introduced into the process by the isomerization unit 250. In some embodiments, the para-ethyltoluene is separated from the para-xylene in the adsorptive separation unit 216 or in extract column 224. In some embodiments, the para-ethyltoluene is removed from the para-xylene product using techniques known in the art.

In one embodiment, the bottoms para-xylene stream 276 comprises about 95.0 weight percent para-xylene. In one embodiment, the bottoms para-xylene stream 276 comprises about 99.2 weight percent para-xylene. In one embodiment, the bottoms para-xylene stream 276 comprises about 99.7 weight percent para-xylene. In one embodiment, the bottoms para-xylene stream 276 comprises about 99.9 weight percent para-xylene. In one embodiment, the bottoms para-xylene stream 276 comprises greater than about 99.9 weight percent para-xylene.

Figure 3:
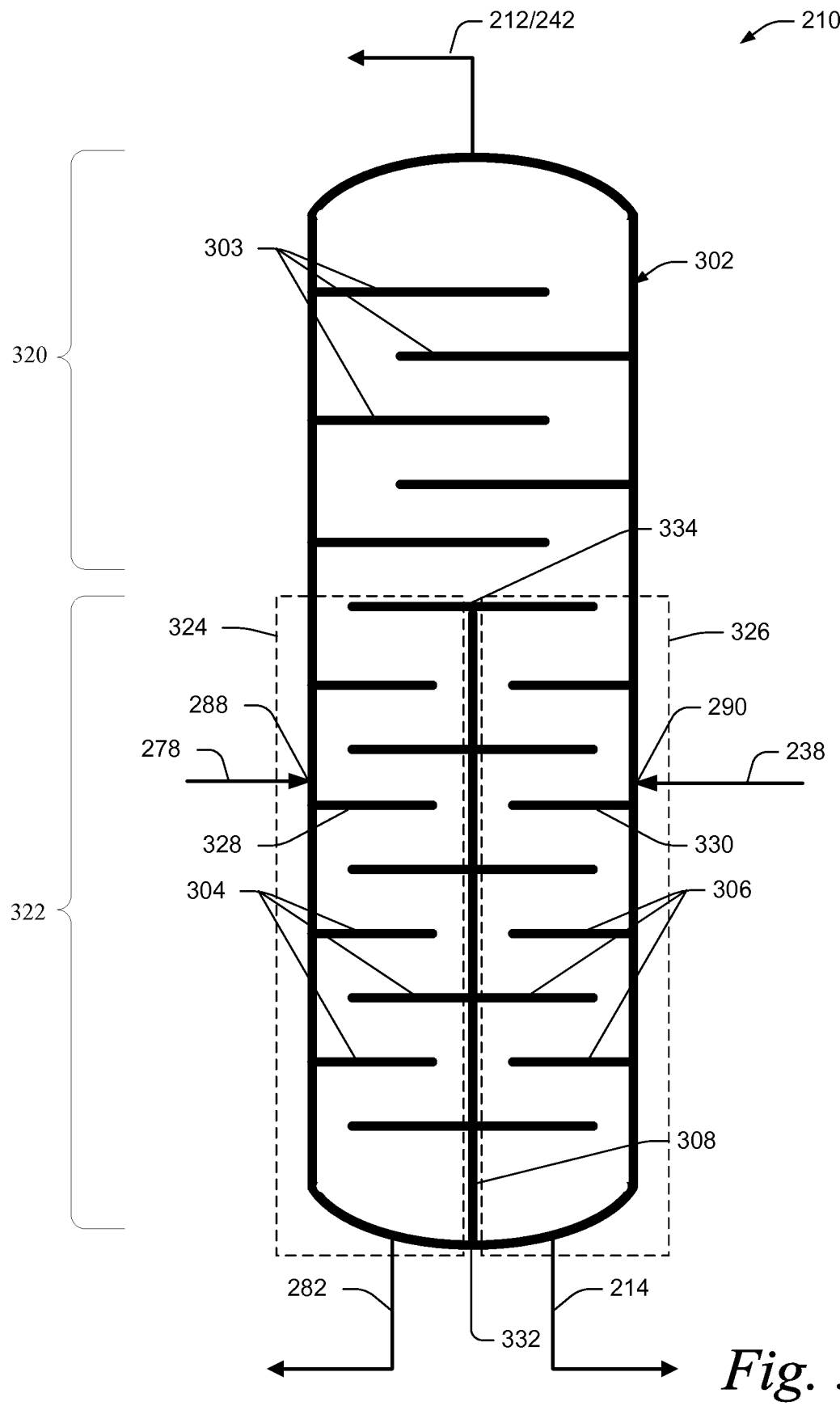
FIG. 3 is a schematic view of one embodiment of Applicant's split fractionation column.

FIG. 3 illustrates Applicant's split fractionation column 210. Split fractionation column 210 comprises housing 302, an upper portion 320, and a lower portion 322. Upper portion 320 includes trays 303 that are similar to a prior art fractionation column. Lower portion 322 is divided lengthwise by partition 308, which extends upwardly from the bottom 332 of column 302 to top portion 334, to create lower distillation zones 324 and 326. Each of the lower distillation zones 324 and 326 have trays 304 and 306, respectively.

Input 278 is introduced into lower distillation zone 324. Input 278 comprises a mixture of C8 aromatics, C9+ aromatics, and toluene.

Input 238 is introduced into the lower distillation 326. Input 238 comprises a mixture of C8 aromatics and toluene. In one embodiment, input 238 comprises a high concentration of para-xylene.

In one embodiment, the para-xylene concentration of input 238 is higher than the para-xylene concentration of input 278. Combining the material from input 278 and 238 into a single stream for fractional distillation in a prior art column (i.e., a column without the upper and lower portions 320 and 322) would result in the undesirable dilution of the high purity material in input 238. In addition, such combining would introduce undesirable C9+ aromatics into the process of FIG. 2.

The partition 308 prevents the liquid in the lower distillation zones from mixing. The partition 308 extends upwardly from the bottom 332 of column 302 to top portion 334. The top 332 of partition 308 is determined by a particular application, but is selected to prevent the mixing of the bottoms liquid products 282 and 214.

The lighter components (i.e., those with a lower boiling point) introduced in inputs 278 and 238 vaporize at the temperature of the lower portion 322. As such, the lighter components travel upwardly in column 302. In one embodiment, the toluene is extracted as a liquid at a side cut tray (not shown) and light ends are extracted as a vapor at the overhead stream 212/242. In another embodiment, the toluene is extracted as a vapor in the overhead stream and condensed to form a liquid stream.

In one embodiment, the stream 212/242 comprises high purity toluene. In one embodiment, the stream 212/242 comprises toluene and light impurities.

The heavier components (i.e., those with a higher boiling point) will remain in liquid form and, therefore, will remain in the lower distillation zone 324, if introduced by way of input 278, or will remain in lower distillation zone 326, if introduced by way of input 238. As such, the heavy fractions of the input 278 and input 238 will remain segregated in the lower portion 322.

In one embodiment, the bottoms product 282 is a mixture of C8 aromatics, C9+ aromatics, and heavies. As shown in FIG. 2, the bottoms product 282 is fed into a xylene fractionation column 204.

In one embodiment, the bottoms product 214 comprises a stream of high purity para-xylene. As shown in FIG. 2, the bottoms product 214 is fed into an adsorption separation unit 234.

The number of trays 303, 304 and 306 in each of the upper portion 320, lower distillation zone 324, and lower distillation zone 326, respectively, vary with the particular product inputs and desired outputs, as would be appreciated by those skilled in the art. In one embodiment, the number of trays in lower distillation zone 324 is different than the number of trays in lower distillation zone 326. In one embodiment, the number of trays in lower distillation zone 324 is the same as the number of trays in lower distillation zone 326.

The locations of inputs 278 and 238 on column 302 are selected to prevent any mixing of the heavy fractions across partition 308. In one embodiment, the partition 308 extends 4 trays above the highest of feed trays 328 and 330. In one embodiment, the partition extends greater than 4 trays above the highest of feed trays 328 and 330. In one embodiment, the partition extends less then 4 trays above the highest of feed trays 328 and 330.

As those skilled in the art will appreciate, Applicant's split fractionation column 300 may be used to separate any two input streams that share a common light fraction but different heavy fractions.

By incorporating Applicant's split fractionation column 302 into the apparatus and process of FIG. 2, the need for a separate toluene fractionation column in communication with aromatic conversion unit 280 is negated. Rather, the split fractionation column 210 is used to extract the toluene from a mixture of heavies for both the xylene separation process and for the aromatic conversion process.

Referring to the foregoing paragraphs, this invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the invention is described through the above-described exemplary embodiments, it will be understood by those of ordinary skill in the art that modifications to, and variations of the illustrated embodiments may be made without departing from the inventive concepts disclosed herein. For example, although some aspects of separating para-xylene has been described, those skilled in the art should readily appreciate that functions, operations, decisions, etc., of all or a portion of each step, or a combination of steps, of the series of steps described may be combined, separated into separate operations or performed in other orders. Moreover, while the embodiments are described in connection with various illustrative processes, one skilled in the art will recognize that the methods and processes described herein can be embodied using a variety of techniques. Furthermore, disclosed aspects, or portions of these aspects, may be combined in ways not listed above. Accordingly, the invention should not be viewed as being limited to the disclosed embodiment(s). The scope of the invention should be determined with reference to the pending claims along with their full scope or equivalents, and all changes which come within the meaning and range of equivalency of the claims are to be embraced within their full scope.

What is claimed is:

1. A process for separating para-xylene from a plurality of xylene isomers, the process comprising:
   introducing at a first feed point a first mixed xylene stream comprising a plurality of xylene isomers into a first adsorptive separation unit to produce a first para-xylene enriched stream and a first raffinate stream;
   introducing a second mixed xylene stream comprising a plurality of xylene isomers into a second adsorptive separation unit to produce a second raffinate stream;
   feeding both said first raffinate stream and said second raffinate stream into a raffinate column;
   producing by said raffinate column a C8 raffinate stream;
   introducing the C8 raffinate stream into an isomerization unit to produce said second mixed xylene stream, and a drag stream in fluid communication with an aromatic conversion unit;
   generating a mixture of aromatic compounds by said aromatic conversion unit;
   introducing an extract stream from said second adsorptive separation unit into first input of a split extract column comprising an internal partition defining a first distillation zone and a second distillation zone, said split extract column comprising said first input for said first distillation zone, a second input for said second distillation zone, a first output for said first distillation zone, a second output for said second distillation zone; and
   introducing said mixture of aromatic compounds in said second input of said split extract column.

2. The process of claim 1, further comprising:
   forming a third mixed xylene stream in said split extract column, wherein said third mixed xylene stream comprises a greater concentration ofpara-xylene than said first mixed xylene stream or said second mixed xylene stream; and
   introducing said third mixed xylene stream into said first adsorptive separation unit at a second feed point.

3. The process of claim 1, wherein:
   the first raffinate stream enters the raffinate column at a first location;
   the C8 raffinate stream exits the raffinate column at a second location;
   the second raffinate stream enters the raffinate column at a third location; and
   wherein the second location is disposed between the first location and the third location.

4. The process of claim 3, further comprising introducing said first enriched para-xylene stream into a first extract column.

5. The process of claim 3, further comprising introducing an output stream from the first extract column into a finishing column to produce a para-xylene product stream.

6. The process of claim 5, further comprising:
   introducing into a xylene fractionation unit a mixture of C8+ aromatic compounds from said second output of said split extract column;
   introducing a plurality of aromatic compounds into said xylene fractionation unit; and
   providing from said xylene fractionation unit said first mixed xylene stream.

7. The process of claim 1, wherein the first adsorptive separation unit utilizes a heavy desorbent and the second adsorptive separation unit utilizes a light desorbent.

* * * * *